United States Patent
Kenyon et al.

(10) Patent No.: US 9,131,936 B2
(45) Date of Patent: Sep. 15, 2015

(54) ANCHOR TIP ORIENTATION DEVICE AND METHOD

(75) Inventors: Mark D. Kenyon, Ringoes, NJ (US); Jessica Liberatore, Union City, CA (US); Daniel J. Smith, Dayton, NJ (US)

(73) Assignee: Ethicon, Inc., Somerville, NJ (US)

( * ) Notice: Subject to any disclaimer, the term of this patent is extended or adjusted under 35 U.S.C. 154(b) by 206 days.

(21) Appl. No.: 13/157,546

(22) Filed: Jun. 10, 2011

(65) Prior Publication Data
US 2012/0316577 A1 Dec. 13, 2012

(51) Int. Cl.
*A61B 17/04* (2006.01)
*A61B 17/00* (2006.01)

(52) U.S. Cl.
CPC ... *A61B 17/0401* (2013.01); *A61B 2017/00336* (2013.01); *A61B 2017/00805* (2013.01); *A61B 2017/00858* (2013.01); *A61B 2017/00907* (2013.01); *A61B 2017/0409* (2013.01); *A61B 2017/0461* (2013.01); *A61B 2017/0464* (2013.01)

(58) Field of Classification Search
USPC .................. 606/139, 142–148, 151, 213, 232
See application file for complete search history.

(56) References Cited

U.S. PATENT DOCUMENTS

| | | | |
|---|---|---|---|
| 5,021,059 A * | 6/1991 | Kensey et al. | 606/213 |
| 5,059,206 A * | 10/1991 | Winters | 606/213 |
| 5,209,737 A | 5/1993 | Ritchart et al. | |
| 5,217,486 A | 6/1993 | Rice et al. | |
| 5,236,445 A | 8/1993 | Hayhurst et al. | |
| 5,456,284 A | 10/1995 | Ryan et al. | |
| 5,540,718 A * | 7/1996 | Bartlett | 606/232 |
| 5,584,860 A | 12/1996 | Goble et al. | |
| 5,683,418 A * | 11/1997 | Luscombe et al. | 606/232 |
| 5,814,051 A | 9/1998 | Wenstrom, Jr. | |
| 5,944,724 A | 8/1999 | Lizardi | |
| 6,068,648 A * | 5/2000 | Cole et al. | 606/232 |
| 6,527,780 B1 * | 3/2003 | Wallace et al. | 606/108 |
| 6,863,671 B1 | 3/2005 | Strobel et al. | |
| 6,981,983 B1 | 1/2006 | Rosenblatt et al. | |
| 7,510,549 B2 | 3/2009 | Rue et al. | |
| 7,896,897 B2 | 3/2011 | Gresham et al. | |
| 8,133,257 B2 * | 3/2012 | Cook et al. | 606/232 |
| 2002/0004668 A1 * | 1/2002 | Bartlett | 606/232 |
| 2002/0087188 A1 * | 7/2002 | Pedlick et al. | 606/232 |
| 2003/0105489 A1 * | 6/2003 | Eichhorn et al. | 606/232 |
| 2004/0093061 A1 * | 5/2004 | Acosta et al. | 623/1.11 |
| 2005/0131349 A1 | 6/2005 | Albrecht et al. | |
| 2005/0171562 A1 * | 8/2005 | Criscuolo et al. | 606/151 |
| 2005/0199249 A1 | 9/2005 | Karram | |
| 2005/0216028 A1 | 9/2005 | Hart et al. | |
| 2005/0240222 A1 * | 10/2005 | Shipp | 606/219 |
| 2006/0287673 A1 * | 12/2006 | Brett et al. | 606/213 |
| 2007/0244426 A1 | 10/2007 | Hart et al. | |
| 2008/0109037 A1 * | 5/2008 | Steiner et al. | 606/232 |
| 2008/0228193 A1 | 9/2008 | Mattityahu | |
| 2009/0209804 A1 | 8/2009 | Seiler et al. | |

* cited by examiner

*Primary Examiner* — Dianne Dornbusch

(57) ABSTRACT

A surgical device for inserting an anchor, including a handle having an actuator, an outer barrel shaft extending from the handle to a distal end and having a channel therethrough, and an outer barrel tip the distal end thereof having an elastomeric septum, a drive pin within the channel, and an implantable anchor removably coupled to the drive pin. The outer barrel shaft is coupled to an actuator for movement between a first extended position wherein the outer barrel shaft tip substantially cover the anchor, and a second retracted position where the outer barrel shaft tip do not cover the anchor. When the shaft is in the first position, the elastomeric septum of the outer barrel tip circumferentially surrounds and engages the anchor to thereby stabilize the anchor prior to deployment, and when the shaft is in the second position, the elastomeric septum does not engage the anchor.

7 Claims, 5 Drawing Sheets

ANCHOR TIP ORIENTATION DEVICE AND METHOD

FIELD OF THE INVENTION

The present invention relates generally to the field of medical devices and instruments, and more particularly to devices and methods for inserting implantable anchors during surgical procedures.

BACKGROUND

Many different surgical procedures require implantation of anchors and the like for various reasons. For example, some hernia repairs utilize anchors of some type to hold a hernia repair mesh in place during healing. Another example is vaginal vault prolapsed repair, where the vaginal cuff is attached or otherwise secured to tissue within the pelvic cavity, such as the sacrospinous ligament. In one described method for such repairs, the vaginal cuff is secured to the sacrospinous ligament using two surgical anchors that are inserted through the vaginal cuff and ligament using a suitable instrument, with trailing sutures tied together within the vagina.

With this procedure as with many others, proper orientation of the anchor can be critical during implantation. Without proper orientation, the anchor may not deploy properly and may not adequately hold the tissue. The delivery device or instrument must be able to contact and possibly manipulate the tissue prior to deployment of the anchor, all without altering the positioning of the anchor relative to the instrument. This is of particular importance during blind procedures where the surgeon cannot verify relatively positioning prior to implantation. If the orientation changes, the tissue penetrating end may not be aligned properly, requiring unacceptably high tissue penetration forces and/or less than optimal tissue grasping ability. Further, once the tip of the anchor does penetrate the desired tissue plane(s), it must be effectively uncoupled from the delivery device so that it remains in place as the delivery device is retracted from the tissue.

Accordingly, what is needed is an improved device and method for ensuring that proper positioning of an anchor or the like relative to an inserter can be maintained during implantation of the anchor.

SUMMARY OF THE INVENTION

A surgical device for inserting an implantable anchor is provided having a handle including an actuator, an outer barrel shaft extending outwardly from the handle to a distal end and having a channel extending therethrough, a outer barrel tip positioned at the distal end of the outer barrel shaft and having an elastomeric septum therein, a drive pin longitudinally aligned with and positioned within the outer barrel shaft channel, and an implantable anchor removably coupled to a distal end of the drive pin. The outer barrel shaft is coupled to the actuator for movement between a first extended position wherein the outer barrel shaft and outer barrel tip substantially cover the anchor, and a second retracted position where the outer barrel shaft and outer barrel tip do not cover the anchor. When the shaft is in the first position, the elastomeric septum of the outer barrel tip circumferentially surrounds and engages the anchor to thereby stabilize the anchor prior to deployment, and when the shaft is in the second position, the elastomeric septum does not engage the anchor.

In one embodiment the anchor has a tissue penetrating distal end, and may further include a filamentary element coupled to and extending from the anchor. The anchor and filamentary element may be made of an absorbable, biocompatible material, such as polydioxanone.

In yet another embodiment, the anchor has a bore extending therein from a proximal end, with the bore being sized and shaped so as to receive therein and form an interference fit with a distal end of said drive pin.

Also provided is a surgical anchor introducer having a handle, an outer barrel extending outwardly from said handle to a distal tip and having a channel extending therethrough, an elastomeric septum positioned within the distal tip of the outer barrel, an elongated drive pin positioned within the outer barrel, and an implantable anchor coupled to a distal end of the drive pin. The outer barrel shaft is movable relative to the drive pin and anchor between a first position where the outer barrel shaft substantially covers the anchor, and a second position where the outer barrel shaft does not cover the anchor. When the shaft is in the first position, the elastomeric septum circumferentially surrounds and engages the anchor to thereby stabilize the anchor prior to deployment, and when the shaft is in the second position, the elastomeric septum does not engage the anchor.

The anchor may further include a tissue penetrating distal end, and a filamentary element may further be coupled to and extend from the anchor. The anchor and filamentary element may be comprised of an absorbable, biocompatible material, such as polydioxanone.

In yet another embodiment, the anchor has a bore extending therein from a proximal end, with the bore being sized and shaped so as to receive therein and form an interference fit with a distal end of said drive pin The outer barrel may be movable between an extended position in the first position and a retracted position in the second position, and may be so movable by an actuator button coupled thereto and positioned on the handle.

In yet another embodiment, the drive pin may be movable between a retracted position in the first position and an extended position in the second position, and may be so movable by an actuator button coupled thereto and positioned on the handle.

The elastomeric septum may be positioned within an outer barrel tip located at the distal end of the outer barrel.

Also provided is a surgical anchor introducer including a handle, an outer barrel extending outwardly from said handle to a distal tip and having a channel extending therethrough, an elastomeric septum positioned within the distal tip of the outer barrel, an elongated drive pin positioned within the outer barrel, an implantable anchor coupled to a distal end of the drive pin, and a means for moving the outer barrel shaft relative to the drive pin and anchor between a first position wherein the outer barrel shaft substantially covers the anchor, and a second position where the outer barrel shaft does not cover the anchor. When the shaft is in the first position, the elastomeric septum circumferentially surrounds and engages the anchor to thereby stabilize the anchor prior to deployment, and when the shaft is in the second position, the elastomeric septum does not engage the anchor.

These and other objects, features and advantages of the present invention will be apparent from the following detailed description of illustrative embodiments thereof, which is to be read in connection with the accompanying drawings.

DETAILED DESCRIPTION

Figure 1:
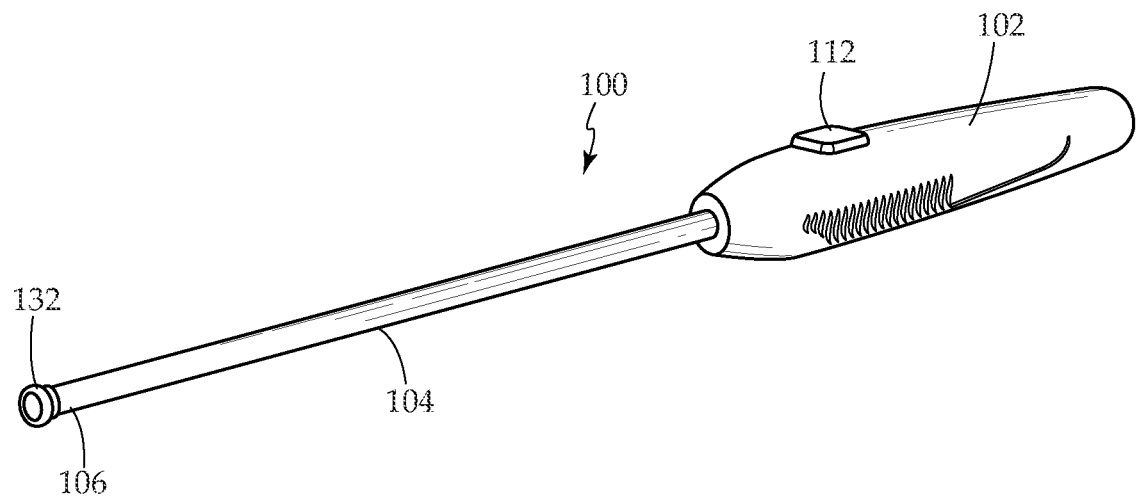
FIG. 1 illustrates one embodiment of an insertion device according to the present invention.
Figure 2A:
FIGS. 2a and 2b are side views of the insertion device of FIG. 1 in the retracted and extended positions respectively.
Figure 2B:
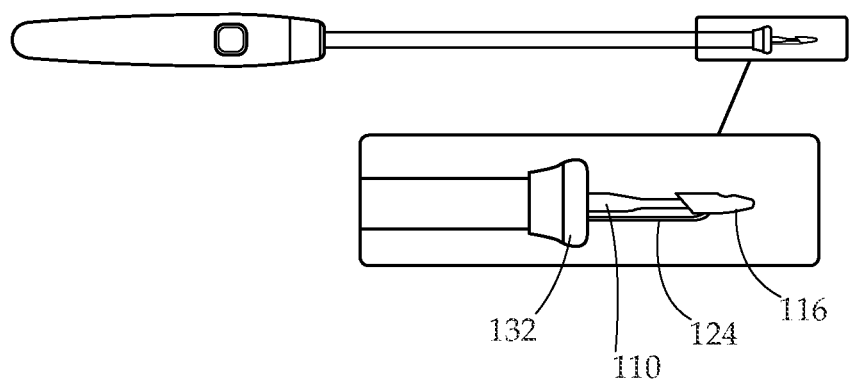
Figure 3:
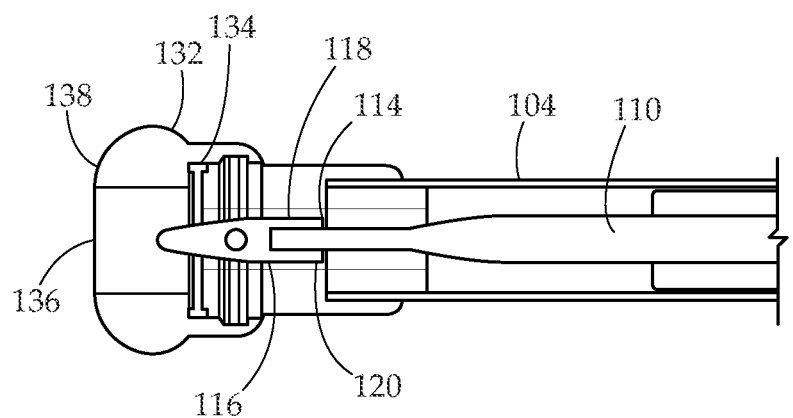
FIG. 3 is an enlarged, cross-sectional view of the distal end of the insertion device of FIG. 1.
Figure 4:
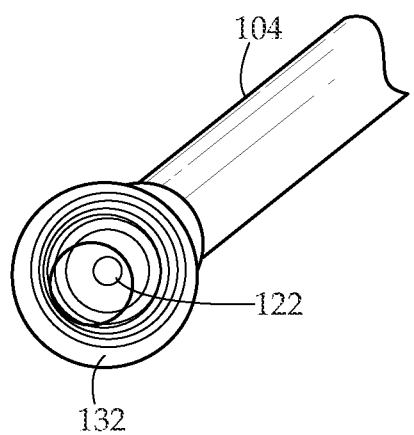
FIG. 4 is an enlarged, perspective view of the distal end of the insertion device of FIG. 1.
Figure 5:
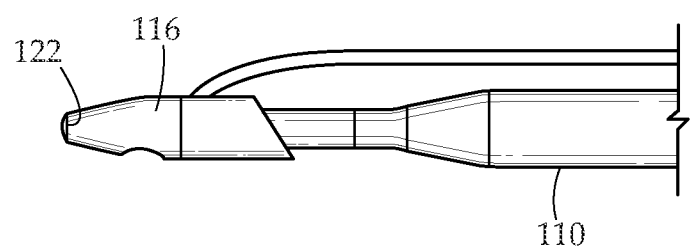
FIG. 5 illustrates how the anchor is mounted on the drive pin within the insertion device of FIG. 1.
Figure 6:
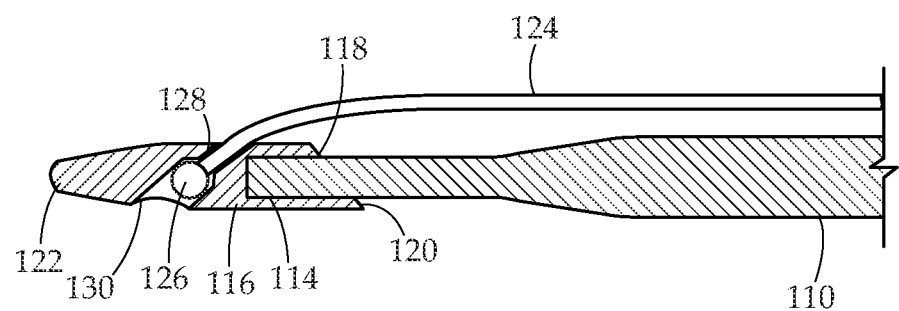
FIG. 6 is a sectional view of FIG. 5.

The insertion device according to the present invention includes a handle 102, and an outer barrel 104 extending outwardly therefrom to a distal end 106. As is best seen in FIG. 3, positioned within the outer barrel 104 is an elongated drive pin 110 with an implantable surgical anchor 116 mounted on its distal end 114. As will be described in further detail below, the outer barrel 104 is movable relative to the drive pin 110 by actuation of button 112 between a first position where the anchor is covered by the outer barrel and outer barrel tip 132 as shown in FIG. 2a, and a second position where the anchor extends distally beyond, and is not covered by, the outer barrel and outer barrel tip as shown in FIG. 2b. Although the outer barrel and outer barrel tip in the illustrated embodiment are separate components, it is to be understood that these elements may also be integrally formed. A channel 118 extending inwardly from the proximal end 120 of the anchor is configured to fit over the distal end 114 of the drive pin as shown in FIG. 6. The channel 118 and distal end 114 of the drive pin are sized and shaped so as to form an interference fit. The distal end 122 of the anchor is tapered, preferably sufficiently to form a tissue penetrating distal end. In the illustrated embodiment, a filamentary element 124 including a distal, bulbous end 126 also is coupled to and extends from the anchor. The filamentary element 124 passes through a second channel 128 extending laterally through the anchor, with the bulbous end of the filamentary element being seated within a larger portion 130 of the channel as shown to thereby prevent the filamentary element from being pulled free from the anchor.

In a preferred embodiment, the anchor is comprised of a size 0 absorbable, biocompatible material such as polydioxanone (PDS). The anchor is approximately 0.299-0.385 inches in length with a maximum outer diameter of approximately 0.080-0.100 inches, and the channel 118 is approximately 0.035 inches in diameter and 0.099-0.137 inches in length. The distal end of the corresponding drive pin preferably has an outer diameter of approximately 0.035+/−0.005 inches so as to form an interference fit, but not so tight as to impede release of the anchor from the drive pin during implantation. The filamentary element 124 is preferably an absorbable, biocompatible material such as polydioxanone, or any other suitable suture material.

As indicated previously, maintaining the positioning of the anchor 116 relative to the drive pin 110 can be critical when trying to implant the anchor. Often the device must be manipulated within the body to ensure implantation of the anchor in the right location. Further, the filamentary element 124 that extends from the anchor remains under slight tension. The frictional fit between the anchor and the distal end of the drive bore is insufficient to prevent the anchor from loosening or becoming slightly askew during manipulation of the delivery device. When out of position, the anchor will not drive straight into tissue as intended when deployed. In some cases, the anchor will turn and jam or break during deployment. Further, if the frictional engagement is too great, deployment of the anchor may become difficult if not impossible.

In order to further stabilize positioning of the anchor prior to implantation, the present invention further includes an outer barrel tip 132 at the distal end of the insertion device. The outer barrel tip extends circumferentially around the distal end 106 of the outer barrel 104, and surrounds and extends distally of the distal tip 122 of the anchor when the insertion device is in first position shown in FIG. 2a. The outer barrel tip includes within it an elastomeric septum 134, which engages the tip of the anchor circumferentially as shown in FIG. 3. The outer barrel tip 132 also preferably includes an opening or channel 136 extending inwardly from the distal end 138 so that the distal tip of the anchor is visible from the distal end of the insertion device. The outer barrel tip may also be comprised of a clear or translucent material so that the anchor position within the tip is readily visible by a user. During deployment, the outer barrel 104 and coupled outer barrel tip 132 is retracted relative to the drive pin 110 and anchor 116 by activating button 112 via any well known means. As this occurs, the anchor drives through the elastomeric septum 132 in the outer barrel tip in a distal direction until the drive pin and anchor are exposed as illustrated in FIG. 2b.

A method of using the insertion device will now be described in detail with reference to FIGS. 7a-7d. This method is an exemplary method, as it is to be understood that the insertion device has application to many other surgical procedures in which implantable anchors are deployed.

Pelvic organ prolapse can sometimes be repaired by attaching the apex of the vagina to the sacrospinous ligament via a vaginal approach rather than requiring surgical incisions. The general nature of this method is described in part in U.S. Pat. No. 6,981,983, which is incorporated herein by reference in its entirety, and an improved procedure is described in co-pending U.S. patent application Ser. No. 13/157,564, filed on Jun. 10, 2011, which is also incorporated by reference herein in its entirety.

Figure 7A:
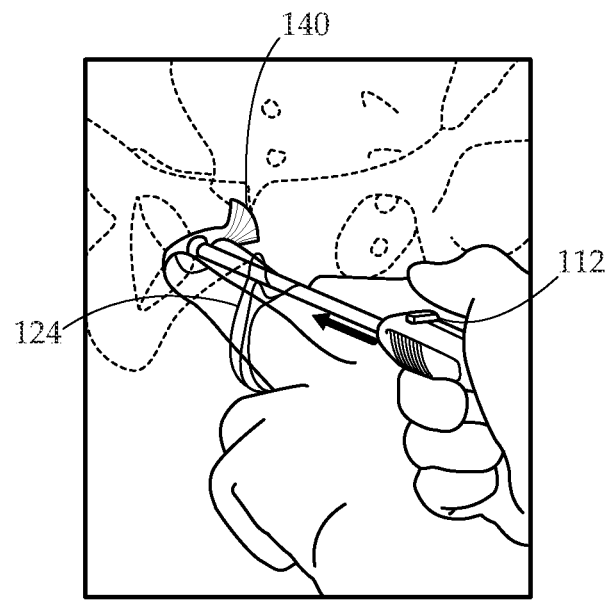
FIGS. 7a-7d illustrate selected steps for using the device of FIG. 1 in an exemplary surgical procedure.
Figure 7B:
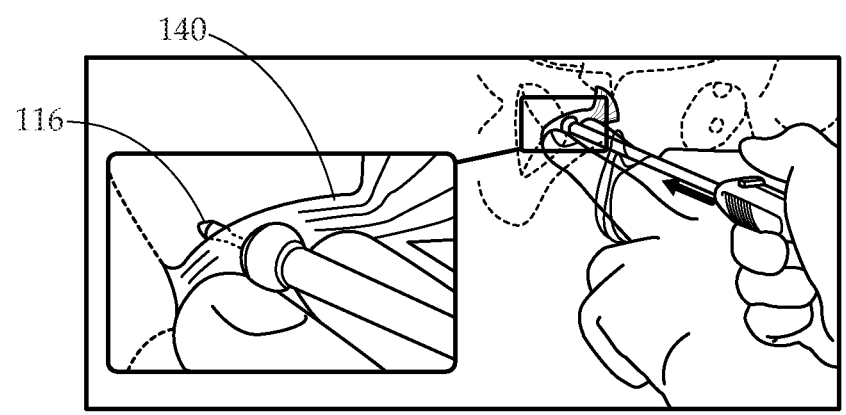
Figure 7C:
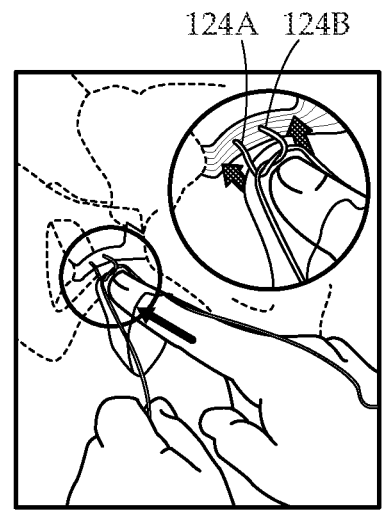
Figure 7D:
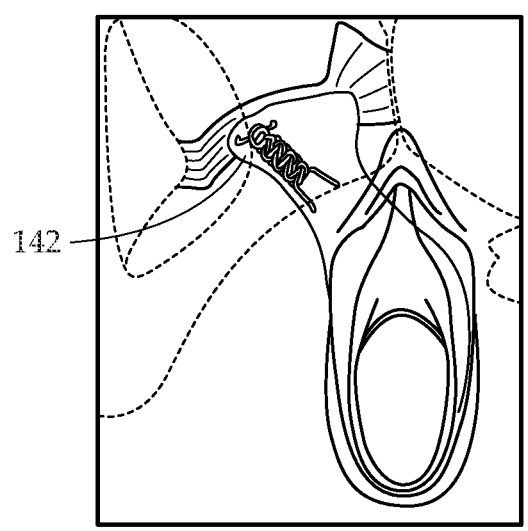

The insertion device of the present invention can be utilized to facilitate these procedures by, via a vaginal route, palpating to find the sacrospinous ligament 140, aligning the distal end of the insertion device with the sacrospinous ligament, and activating the trigger mechanism as illustrated in FIGS. 7a and 7b to deploy the anchor. As illustrated in more detail in the enlarged portion of FIG. 7a, the anchor is deployed entirely through the vaginal wall and sacrospinous ligament 140, allowing the proximal end 102 of the anchor to catch or snag tissue on the far side of the ligament such that tension on the trailing filamentary element will not pull the anchor back through the ligament. For this particular treatment procedure, this can be performed twice with two different anchors in close proximity as shown in FIG. 7c, and the respective trailing filamentary elements 124a, 124b tied together within the vaginal canal to approximate the vaginal apex 142 to the sacrospinous ligament as shown if FIGS. 7c and 7d. The ends may be secured with multiple knots as shown, or fewer if desired. The ends of the filamentary elements are then trimmed, leaving the implantable anchors and knotted filamentary elements in place.

Although illustrative embodiments of the present invention have been described herein with reference to the accompanying drawings, it is to be understood that the invention is not limited to those precise embodiments and that various other changes and modifications may be effected herein by one skilled in the art without departing from the scope or spirit of the invention.

What is claimed is:

1. A surgical device for inserting an implantable anchor, comprising:
   a handle including an actuator;
   an outer barrel shaft extending outwardly from the handle to a distal end and having a channel extending therethrough;
   a outer barrel tip positioned at the distal end of the outer barrel shaft and having an elastomeric septum therein at a location proximal from the distal end of the outer barrel tip;
   a drive pin longitudinally aligned with and positioned within the outer barrel shaft channel;
   an implantable anchor having a tissue penetrating distal end, having a longitudinal axis, having a proximal end the entire surface of which extends at an angle of less than ninety degrees relative to the longitudinal axis, having lateral sides extending between said distal and proximal ends, and having an axial bore extending therein from the proximal end along said longitudinal axis, the axial bore being sized and shaped to receive therein a distal end of said drive pin to thereby removably coupled the drive pin and implantable anchor, and a filamentary element coupled to and extending laterally outward to an exterior of said anchor from a lateral side of the anchor at a location distal of the axial bore;
   wherein the outer barrel shaft is coupled to the actuator for movement between a first extended position wherein the outer barrel shaft and outer barrel tip substantially cover the anchor, and a second retracted position where the outer barrel shaft and outer barrel tip do not cover the anchor, and wherein when the shaft is in the first position, the elastomeric septum of the outer barrel tip circumferentially surrounds and engages the anchor to thereby stabilize the anchor prior to deployment, and wherein when the shaft is in the second position, the elastomeric septum does not engage the anchor.

2. The surgical device according to claim 1, wherein the anchor and filamentary element are comprised of an absorbable, biocompatible material.

3. The surgical device according to claim 2, wherein the anchor and filamentary element are comprised of polydioxanone.

4. A surgical anchor introducer, comprising:
   a handle;
   an outer barrel extending outwardly from said handle to a distal tip and having a channel extending therethrough;
   an elastomeric septum positioned within the distal tip of the outer barrel at a location proximal of a distal end of the distal tip;
   an elongated drive pin positioned within the outer barrel;
   an implantable anchor having a tissue penetrating distal end, having a longitudinal axis, having a proximal end the entire surface of which extends at an angle of less than ninety degrees relative to the longitudinal axis, having lateral sides extending between the distal and proximal ends, and having an axial bore extending therein from the proximal end, the axial bore being sized and shaped to receive therein a distal end of the drive pin to thereby removably couple the drive pin and implantable anchor and a filamentary element coupled to and extending laterally outward to an exterior of said anchor from a lateral side of the anchor at a location distal of the axial bore;
   wherein the outer barrel shaft is movable relative to the drive pin and anchor between a first position wherein the outer barrel shaft substantially covers the anchor, and a second position where the outer barrel shaft does not cover the anchor, and wherein when the shaft is in the first position, the elastomeric septum circumferentially surrounds and engages the anchor to thereby stabilize the anchor prior to deployment, and wherein when the shaft is in the second position, the elastomeric septum does not engage the anchor.

5. The introducer according to claim 4, wherein the anchor and filamentary element are comprised of an absorbable, biocompatible material.

6. The introducer according to claim 5, wherein the anchor and filamentary element are comprised of polydioxanone.

7. The introducer according to claim 4, wherein the outer barrel is movable between the extended and retracted positions by an actuator button coupled thereto and positioned on the handle.

* * * * *